United States Patent [19]

Becker et al.

[11] Patent Number: 5,002,971

[45] Date of Patent: Mar. 26, 1991

[54] METHOD AND AGENT FOR CONTROLLING THE PEACH TWIG BORER

[75] Inventors: Rainer Becker, Bad Duerkheim; Ernst Buschmann, Ludwigshafen; Wolfgang Mackenroth, Bad Duerkheim; Gregor Schuermann, Heidelberg; Walter Seufert, Speyer; Wolfgang Seppelt, Bobenheim-Roxheim; Wolfgang Krieg, Weingarten; Ulrich Neumann, Schifferstadt, all of Fed. Rep. of Germany

[73] Assignee: BASF Aktiengesellschaft, Ludwigshafen, Fed. Rep. of Germany

[21] Appl. No.: 310,901

[22] Filed: Feb. 16, 1989

[30] Foreign Application Priority Data

Feb. 24, 1988 [DE] Fed. Rep. of Germany ....... 3805751

[51] Int. Cl.$^5$ .................. A01N 37/06; A01N 31/00
[52] U.S. Cl. .................................. 514/549; 514/739
[58] Field of Search ................... 514/549, 739

[56] References Cited

PUBLICATIONS

Roelofs et al.: *Environmental Entomology*, 4, No. 4, pp. 580–582 (1975).
Rice et al., *Journal of Economic Entomology*, 68, 358–360, 1975.
Odinokov, et al., *Chemical Abstracts*, 104, No. 11, 17 Mar. 1986, 88333k.

*Primary Examiner*—John W. Rollins
*Attorney, Agent, or Firm*—Oblon, Spivak, McClelland, Maier & Neustadt

[57] ABSTRACT

Agent for controlling the peach twig borer, Anarsia lineatella, by the confusion technique containing a mixture of E5-decen-1-ol (I), E5-decen-1-yl acetate (II) and Z5-decen-1-ol (III) and Z5-decen-1-yl acetate (IV), the amount of the Z isomers (III) and (IV) being up to 50% by weight, based on the mixture (I) to (IV), and, if required, conventional additives and assistants.

14 Claims, No Drawings

METHOD AND AGENT FOR CONTROLLING THE PEACH TWIG BORER

The present invention relates to a method and agent for controlling the peach twig borer, *Anarsia lineatella*.

The peach twig borer, *Anarsia lineatella* Zell. from the Gelechiidae family, is common across the paleoarctic region as far as Central Asia, the Balkans and North Africa. In relatively warm countries, such as France, Italy, Spain, Portugal, Israel and Morocco, and in areas of intensive fruit cultivation, *Anarsia lineatella* is a major pest. The host plants include peaches, apricots and almonds and to a lesser extent plums, apples and cherries (Audemard 1974, INRA Publ. No. 20).

In the temperate climate of Central Europe, there are two generations per year. The larvae hibernate, and the moths of the first generation fly in June/July. The caterpillars which hatch from the eggs enter young shoots generally at a leaf base or through a bud and destroy the pith by boring downward (peach twig borer). The larva then leaves the dying shoot and bores into a new one and can thus destroy several shoots.

In arid areas, infestation of the fruit by the caterpillars of the second generation, with flight of the moth in August/September, is of very great economic importance.

To date, the peach twig borer has been controlled unspecifically by the conventional means, i.e. by using insecticides. Following identification of the sexual attractant of the peach twig borer (Roelofs et al., Environm. Entomol. 4 (1975), 580 et seq.), a controlled method could be used.

In the case of butterflies, it is known that female animals ready for mating produce sexual attractants (pheromones) and excrete them into the environment. Male butterflies of the same species can then locate the females with the aid of this scent. Rice and Jones stated in J. Econ. Entomol. 68 (1975), 358–360 that a mixture of 5 mg of E5-decen-1-yl acetate and 1 mg of E5-decen-1-ol has a good attractant action. The pheromone can thus be used in traps.

In principle, there are three different possible methods for using sexual attractants in crop protection: 1. Monitor technique Pheromone traps provided with synthetic sexual attractant lures are suspended in potential areas of infestation. The trapping of male moths indicates the occurrence of the pest. It is also possible to obtain information about the severity of infestation and about the correct time for control. 2. Trapping technique The attractant can be combined with insecticidal active ingredients. It is possible to add insecticides to the lure/the trap or only to treat the immediate vicinity of the trap. As a result, the majority of the male moth population attracted from a long distance can be killed. Pollution of the biotope is reduced to an acceptable level.

3. Confusion technique

Finally, the pest can be controlled by saturating the atmosphere with sexual attractants or substances having a similar action. The male butterflies are prevented from finding the females and mating of the animals is thus prevented. In this case, a relatively large amount of the attractant is distributed in the atmosphere in the entire area of the crop to be protected, so that the males can perceive the presence of scent everywhere, and their normal orientation behavior is disturbed.

The third method (confusion method), in particular, is an extremely selective and also effective method for controlling an undesirable species while protecting the non-target organisms, in particular all useful organisms.

Furthermore, this method requires only relatively small amounts of the active ingredients, these amounts often being only fractions of the usual doses of the traditional insecticidal active ingredients (cf. Birch ed., Pheromones, North Holland Publ. Co., 1974).

Methods 1 and 2 are disadvantageous in that the synthetic attractant must be exactly identical to its natural counterpart in terms of structure and purity (Minks and Voermann, Entomologia exp. and appl. 16 (1973), 341–349 and Wegler, Chemie der Pflanzenschutzund Schädlingsbekämpfungsmittel Vol. 6 (1981), page 167). Industrial mixtures or the like have regularly failed in trapping experiments. From the experience gained with methods 1 and 2, it was to be assumed that method 3 too would only be feasible with very pure pheromones of the peach twig borer. However, the preparation of very pure pheromones requires expensive separation operations, such as preparative gas chromatography over an Ag-coated carrier, so that a material prepared in this manner does not permit economical use over a large area.

It is an object of the present invention to provide an agent for controlling the peach twig borer, which permits economical use over a large area and in particular makes it possible to ensure control of the pest by the confusion method described above, without the additional use of traditional insecticides.

We have found that this object is achieved by an agent for controlling the peach tree borer, *Anarsia lineatella*, containing a mixture of E5-decen-1-ol (I), E5-decen-1-yl acetate (II) and Z5-decen-1-ol (III) and Z5-decen-1-yl acetate (IV), the amount of the Z isomers (III) and (IV) being up to 50% by weight, based on the mixture (I) to (IV).

Advantageous mixtures are those in which the amount of the Z isomers (III) and (IV) is from 1 to 35, in particular from 1 to 25, preferably from 2 to 20, % by weight, based on the mixture (I) to (IV).

The novel agents advantageously contain from 1 to 50% by weight of E5-decen-1-ol (I) and from 50 to 99% by weight of E5-decen-1-yl acetate (II), the percentages in each case being based on (I)+(II), and from 1 to 50% by weight of Z5-decen-1-ol (III) and from 50 to 99% by weight of Z5-decen-1-yl acetate (IV), the percentages in each case being based on (III)+(IV).

Preferred agents are those in which the ratio of acetate (II) to alcohol (I) is 50:50, in particular 65:35, particularly preferably 80:20. Corresponding ratios are preferred for the Z isomers (III) and (IV).

In view of the publications by Wegler and Minks and Voermann (loc. cit.), it was surprising that, in experiments using the confusion technique, mating of the females is virtually completely absent owing to the disturbance of the orientation of the males, described above, even when the E/Z mixtures are used, especially since it is known that even pure isomeric pheromones identical to the natural ones are not always suitable for preventing mating by the confusion method, because other factors, for example optical orientation even in the pheromone-treated field, permit the sexes to find one another (cf. for example M. Kehat et al., Phytoparasitica 13 (3-4), 215–220).

The preparation of the compounds (I), (II), (III) and (IV) is described, for example, by M. S. Chadha et al., Indian J. Chem. 22B (1983), 1221–1223, S. Warren, Tetrahedron Lett. 25 (1984), (3), 357–360 or V. N. Odinokov et al., Chem. Nat. Comp. 21 (1985), 369–371.

The starting materials generally used are the corresponding alkynols, which can be reduced to the trans- or cis-alkenol in a conventional manner (P. I. Suirshaya, C. C. Leznoff, J. Waetherslon and J. E. Lang, J. Chem. Eng. Data 24 (1979), (2), 152–155, and C. Henrick, Tetrahedron 33 (1977), 1845). Conversion into the corresponding acetates can be effected in a conventional manner, for example with acetyl chloride or acetic anhydride in the presence of pyridine, triethylamine or a similar base.

The industrial preparation of the novel mixtures can advantageously be carried out by a procedure in which the tetrahydropyranyl ether of hex-5-yn-1-ol, in liquid ammonia and in the presence of lithium amide as a base, is alkylated with n-butyl bromide, and the crude product is hydrogenated over a Pd/CaCO$_3$ catalyst (quinoline-poisoned) (W. Roelofs et al., Environ. Entomol. 4 (1975), (4) 580–582). After acidic elimination of the tetrahydropyranyl radical, the Z5-decenol is subjected to a photochemical rearrangement reaction to give an E/Z-decenol mixture, the amount of the E isomer generally being from 50 to 80% by weight, based on the E/Z mixture, and acetylation is then carried out. This photoisomerization is described in, for example, German Laid-Open Application DOS 3,417,943. The alcohols are then converted into the acetates (cf. Chem. Nat. Comp. 21 (1985), 369–371).

The agent can be used together with conventional assistants, for example appropriately prepared strips of plastic or string, attractant-filled ampoules or the like, and may also contain other impurities from the preparation.

The active ingredient can be formulated as both liquid and solid preparations. Suitable solvents are high boiling, aromatic, aliphatic or cycloaliphatic compounds. In addition to hydrocarbons, esters, ethers and ketones are also particularly suitable. Typical members of these classes are, for example, xylene, methylnaphthalenes, liquid paraffins, cyclohexanone, ethylglycol acetate, isophorone and dibutyl phthalate. These solvents can be used alone or as a mixture with other components. The saturated $C_{10}$-esters corresponding to the compounds (III) or (IV), and homologs of the said esters, are particularly suitable formulation assistants and may be regarded as synergistic agents since they reinforce the action of (I), (II), (III) and (IV).

Furthermore, solutions in vegetable, animal or synthetic oils or fats and other evaporation-inhibiting solvents having a low vapor pressure, e.g. dioctyl phthalate, can be prepared for prolonging the action.

It is also possible to bind the active ingredient in or on natural or synthetic solid carriers, such as rubber, cork, cellulose, plastics, ground coal, sawdust, silicates, pumice, calcined clay or similar solid carriers, or to use the active ingredient in special capsule formulations or plastic containers in order to achieve uniform release into the atmosphere over prolonged periods. The active ingredient can also be evaporated from suitable containers (capillaries or other vessels), through narrow orifices or by diffusion through the container wall, with the result that particularly uniform scent concentrations are achieved over prolonged periods, and from multilayer plastic flakes.

The content of active ingredient in these formulations may vary within wide limits. In general, the ratio of active ingredient to additive may be, for example, from 10:1 to 1:10$^3$. In capsule formulations or other suitable containers, the active ingredient can be used, for example, in pure, undiluted form, and its proportion by weight, based on the total formulation, can be very high, i.e. up to 90%. In general, however, very low concentrations of active ingredient in the formulations are sufficient to achieve the desired effect on Anarsia males. An active ingredient/additive ratio of from 1:3 to 1:10$^2$, in particular from 1:10 to 1:100, is preferred.

The active ingredient can also be applied in comparatively high concentrations in order to disorientate and confuse the males and thus prevent them from mating. Formulations which are most suitable for this method are those containing sparingly volatile additives which release the active ingredient over a prolonged period, such as rubber, wadding, waxes, polymers or evaporation-inhibiting, sparingly volatile oils or paraffins, and formulations in capsules or other containers (capillaries), which release the attractant either through their wall or through narrow orifices (cf. EP-A 256 549 or 281 918).

The experiments described below show the applicability of the agents described for controlling the peach twig borer.

The following abbreviations are used:

| | |
|---|---|
| E5-decen-1-ol | E5-10-OH (I) |
| E5-decen-1-yl acetate | E5-10Ac (II) |
| Z5-decen-1-ol | Z5-10-OH (III) |
| Z5-decen-1-yl acetate | Z5-10Ac (IV) |

EXPERIMENTS 1 TO 4

In an area infested with peach twig borer, pheromone-impregnated PVC strips were suspended on a plot having the size stated in Table 1. The number of dispensers was 500/ha and the amount of active ingredient was 45 g/ha.

Active ingredient composition: 77% by weight of E5-10Ac, 3% by weight of Z5-10Ac, 19% by weight of E5-10-OH and 1% by weight of Z5-10-OH.

Test location: St. Marcel les Valence, France
Dates of application: May 6, June 3, June 25 and July 10 1985
About 130 peach trees per 0.25 ha Evaluation was effected by the monitor technique, in which an attractant trap provided with a rubber tube lure impregnated with 10 mg of E5-10Ac and 2 mg of E5-10-OH was suspended in the foliage of the tree in the treated plot as well as in an untreated control plot of 0.25 ha, and the number of male moths found sticking to the adhesive surface placed in the trap was counted.

The results are summarized in Table 1.

TABLE 1

| Experiment number | 1 | 2 | 3 | 4 |
|---|---|---|---|---|
| Plot size (ha) | 0.25 | 1 | 0.75 | 1 |
| Catch in the treated plot | 0 | 11 | 14 | 7 |

In contrast, 130 moths were trapped in the control plot of 0.25 ha. No fruit was infested in the treated plot (0.25 ha), whereas 10 fruits/tree showed damage in the control plot.

EXPERIMENTS 5 AND 6

Dispenser: Polyethylene ampoules containing pheromone

Number of dispensers: 500/ha

Application rate: 200 g/ha

Active ingredient: 67% by weight of E5-10Ac, 13% by weight of Z5-10Ac, 15% by weight of E5-10-OH and 5% by weight of Z5-10-OH Test locations: Avignon (5), St. Marcel les Valence (6)

Dates of application: April 22 and June 30 1986

The evaluation was carried out similarly to Experiments 1 to 4, and the results are summarized in Table 2:

TABLE 2

| Exeriment number | 5 | 6 |
|---|---|---|
| Plot size (ha) | 2 | 1 |
| Catch in the treated plot | 6 | 0 |

In contrast, 75 moths were trapped in the control plot of 1 ha.

We claim:

1. A method for controlling the peach twig borer (*Anarsia lineatella*) in a crop-containing area by the confusion method, which comprises dispersing an effective amount of a mixture of E5-decen-1-ol (I), E5-decen-1-yl acetate (II), Z5-decen-1-ol (III) and Z5-decen-1-yl acetate (IV), the amount of the Z isomers (III) and (IV) being up to 50% by weight, based on the mixture (I) to (IV), in the atmosphere of said crop-containing area.

2. The method according to claim 1, wherein the amount of the Z isomers (III) and (IV) is from 1–35% by weight, based on the mixture (I) to (IV).

3. The method according to claim 1, wherein said mixture comprises from 1–50% by weight of E5-decen-1-ol (I) and from 50–99% by weight of E5-decen-1-yl acetate (II), the percentages in each case being based on (I)+(II), and from 1–50% by weight of Z5-decen-1-ol (III) and from 50–99% by weight of Z5-decen-1-yl acetate (IV), the percentages in each case being based on (III)+(IV).

4. The method according to claim 1, wherein the amount of Z isomers (III) and (IV) is from 1–25% by weight, based on the mixture (I) to (IV).

5. The method according to claim 4, wherein the amount of Z isomers (III) and (IV) is from 2–20% by weight, based on the mixture (I) to (IV).

6. The method according to claim 4, wherein said mixture further comprises a carrier.

7. The method according to claim 6, wherein said carrier is a liquid or a solid carrier.

8. The method according to claim 7, wherein said liquid carrier is an evaporation-inhibiting solvent having a low vapor pressure, which prolongs the action of the agent.

9. The method according to claim 7, wherein said liquid carrier is one or more saturated $C_{10}$-esters corresponding to compounds (III) or (IV) or the homologs thereof.

10. The method according to claim 6, wherein said mixture of compounds (I) to (IV) are used in a ratio of from 10:1 to $1:10^3$ relative to said carrier.

11. The method according to claim 1, wherein the ratio of acetate (II) to alcohol (I) is 50:50.

12. The method according to claim 11, wherein the ratio of acetate (II) to alcohol (I) is 65:35.

13. The method according to claim 1, wherein said mixture is 77% by weight of E5-decen-1-yl acetate, 3% by weight of Z5-decen-1-yl acetate, 19% by weight of E5-decen-1-ol and 1% by weight of Z5-decen-1-ol.

14. The method according to claim 1, wherein said mixture is 67% by weight of E5-decen-1-yl acetate, 13% by weight of Z5-decen-1-ol, 15% by weight of E5-decen-1-ol and 5% by weight of Z5-decen-1-ol.

* * * * *